United States Patent
Krylov et al.

(10) Patent No.: US 7,087,640 B2
(45) Date of Patent: Aug. 8, 2006

(54) SUBSTANCE WITH SEDATIVE EFFECT

(75) Inventors: Boris Vladimirovich Krylov, selo Pavlovo (RU); Boris Fedorovich Shchegolev, St.-Petersburg (RU)

(73) Assignee: Technology Commercialization Corp, New York, NY (US)

( * ) Notice: Subject to any disclaimer, the term of this patent is extended or adjusted under 35 U.S.C. 154(b) by 398 days.

(21) Appl. No.: 10/389,538

(22) Filed: Mar. 14, 2003

(65) Prior Publication Data

US 2003/0181516 A1     Sep. 25, 2003

(30) Foreign Application Priority Data

Mar. 19, 2002 (RU) .............................. 2002107079

(51) Int. Cl.
*A61K 31/35* (2006.01)
(52) U.S. Cl. ..................................... 514/455; 514/456
(58) Field of Classification Search ................ 514/455, 514/456
See application file for complete search history.

(56) References Cited

U.S. PATENT DOCUMENTS

| | | | |
|---|---|---|---|
| 1,782,111 A | 11/1930 | Adams | |
| 1,796,977 A | 3/1931 | Bailey | |
| 3,706,831 A | 12/1972 | Plotnikoff | |
| 3,710,795 A | 1/1973 | Higuchi | |
| 3,742,951 A | 7/1973 | Zaffaroni | |
| 3,797,494 A | 3/1974 | Zaffaroni | |
| 4,115,567 A | 9/1978 | Doria | |
| 4,117,161 A | 9/1978 | Pozuelo | |
| 4,124,715 A | 11/1978 | Pozuelo | |
| 4,198,426 A | 4/1980 | Philipp | |
| 4,221,890 A | 9/1980 | Dimmick | |
| 4,276,890 A | 7/1981 | Fichera | |
| 4,311,691 A | 1/1982 | Fichera | |
| 4,325,952 A | 4/1982 | Silvestrini | |
| 4,568,343 A | 2/1986 | Leeper | |
| 4,575,502 A | 3/1986 | Hider | |
| 4,696,818 A | 9/1987 | Kim | |
| 4,786,653 A | 11/1988 | Golwyn | |
| 4,788,189 A | 11/1988 | Glazer | |
| 4,866,052 A * | 9/1989 | Hider et al. ................ | 514/184 |
| 5,219,858 A | 6/1993 | Parnell | |
| 5,411,985 A | 5/1995 | Bills | |
| 5,470,873 A | 11/1995 | Yoon | |
| 5,506,268 A | 4/1996 | Balandrin | |
| 5,589,182 A * | 12/1996 | Tashiro et al. .............. | 424/423 |
| 5,646,179 A | 7/1997 | Muller-Kuhrt | |
| 5,888,993 A | 3/1999 | McNell | |
| 2003/0211180 A1 * | 11/2003 | Cheng et al. ............... | 424/741 |

FOREIGN PATENT DOCUMENTS

| | | | |
|---|---|---|---|
| JP | 53-18739 | | 2/1978 |
| RU | 2178303 | | 1/2002 |
| WO | WO 92/13850 | | 8/1992 |
| WO | WO9714414 | * | 4/1997 |
| WO | WO9907413 | * | 2/1999 |

OTHER PUBLICATIONS

Napoli V., Treatment of postoperative pain in foot surgery., Database EMBASE, AN:96268834 (abstract only) Chirurgia del Piede, 1996, vol. 20(No. 1), pp. 39-42.*

Durg information, Opium Poppy, Herbs2000.com,Database from GOOGLE.com, (http://herbs2000.com/herbs/herbs_poppy_opium.htm.*

Drug information, POPP, white, Botanical.com, Data base form GOOGLE. com.*

ICTFM base, drug information on Papaver Somniferm L., Database from GOOGLE.com.*

Felter HW, Lloyd Ju Opium (U.S.P.)—Opium, from King's American Dispensatory, 1898. Printout of the Internet site www.ibiblio.org, 17 pages, Nov. 20, 2003.

Krylov BV, Derbenev AV, Podzorova SA, et al. Morphine decreases the voltage sensitivity of slow sodium channels. Neuroscience and Behavioral Physiology vol. 30, No. 4, 2000, pp. 431-439, Kluwer Academic/Plenum Publishers.

(Continued)

*Primary Examiner*—Vickie Kim
(74) *Attorney, Agent, or Firm*—Boris Leschinsky

(57) ABSTRACT

A substance with sedative effect comprises a therapeutically effective amount of a gamma-pyrone such as comenic acid, meconic acid, chelidonic acid, and alike in a pharmaceutically acceptable carrier. When administered at a daily dosage of between 5 and 200 mg of active ingredient per kilogram of a body weight of a patient, the substance can be used to treat various neurotic disorders such as insomnia, anxiety, neurosis, depression as well as withdrawal symptoms for drug addiction patients, especially for patients addicted to opioid-based drugs. The substance can be delivered in a number of ways of systemic administration of a pharmaceutical agent including oral, parenteral, transdermal, and transmucosal administration. For drug addicted patients, the preferred method of administration involves a subcutaneous implant providing a continuous release of an active ingredient at an effective daily rate over the entire treatment period ranging from 5 to 30 days, and preferably from 13 to 20 days.

7 Claims, No Drawings

OTHER PUBLICATIONS

Plakhova VB Shchegolev BF, Rogachevskii IV et al. A possible molecular mechanism for the interaction of defensin with the sensory neuron membrane. Neuroscience and Behavioral Physiology vol. 32, No. 4, 2002, pp. 409-415, Plenum Publishing Corp.

Krylov BV, Bagraev NT, Klyachkin Le et al. Chemical and infrared light induced effects on the voltage sensitivity of slow sodium channel. Proceedings of SPAS, vol. 4, pp. A38-A39, Jun. 12-17, 2000, St. Peterburg, RUSSIA.

Krylov BV, Podzorova SA, Vilin YY. Inactivation kinetics of sensory neuron sodium channels depend on the type of hydrogen ion buffer. Neuroscience and Behavioral Physiology vol. 28, No. 1, 1998, pp.65-71, Plenum Publishing Corp.

Derbenev AV, Krylov BV, Shurygin AY. Effects of meconic and comenic acids on slow sodium channels of secondary neurons. Membrane Cell Biology, 2000, vol. 13(3), pp. 379-387.

Hunt SP Mantyh PW. The molecular dynamics of pain control. Nature reviews. Neuroscience. vol. 2, Feb. 2001, pp. 83-91.

Palmer AM, Carter N. The role of sodium channels in disease . The Newsletter for the Society for Medicines Research. Jan. 2002, vol. 8, Issue 1, pp. 1-14.

Jensen TS, Gottrup H, Kasch H et al. Has basic research contributed to chronic pain treatment? Acta Anaesthesiologica Scandinavica, 2001, 45, pp. 1128-1135.

Xie Z. Ouabain interaction with cardiac Na/K-ATPase reveals that the enzyme can act as a pump and as a signal transducer. Cellular and Molecular Biology, 2001, 47(2), pp. 383-390.

Krylov BV et al. Ethanol modifyes rat sensory neuron sodium channels. Russian Journal of Physiology, 1999, 85-N-1, pp. 110-118. In Russian with English abstract.

Plakhova VB, Sabanov VS et al. Probable molecular mechanisms of slow sodium channels gating machinery . . . Sensory Systems, vol. 14, No. 1, 2000, pp. 48-59. Published in Russian with English abstract.

Katina IE, Shchegolev BF, Zadina JE, McKee ML, Krylov BV. Endomorphins inhibit currents through voltage-dependent sodium channels. Sensory Systems, vol. 17, No. 1, 2003, pp. 1-17. Published in Russian with English abstract.

* cited by examiner

SUBSTANCE WITH SEDATIVE EFFECT

CROSS-REFERENCE DATA

This application claims foreign priority benefits of a Russian Patent Application No. 2002107079/14 filed Mar. 19, 2002 with the same title.

BACKGROUND OF THE INVENTION

The present invention relates generally to pharmaceutical compounds and methods for their use to cause sedative and analgesic effects in animals and humans. More specifically, the invention relates to the use of gamma-pyrones in pharmaceutically acceptable forms for the treatment of various neurotic disorders. For the purposes of this description, the term "neurotic disorder" includes among others such conditions as anxiety, pain, insomnia, depression, neurosis as well as pain and other symptoms associated with treatment of chemical and drug abuse patients. All of these conditions involve the neurons of the central nervous system.

Sedative compounds known in the art are a chemically varied group of compositions of natural and synthetic origin that predominantly have a tranquilizing effect on the central nervous system. Different sedatives produce different physiological effects. Understanding of these effects is helpful in selectively treating various disorders. This mechanism of action is not always entirely clear but it is believed that sedative drugs in general are intended to cause selective suppression of subcortical (limbus) and cortical brain structures, which regulate emotions.

The mildest examples of sedative drugs include extracts of motherwort, passiflora, valerian root (Tinctura Valeriana), bromides of caustic metals (Kalium bromatum, Natrium bromatum). These drugs typically cause only a light tranquilizing effect on the subject. Stronger tranquilizers are used to lower a patient's anxiety. These are synthetic medicinal preparations, examples of which include derivatives of benzodiazepin (diazepam), diphenyl methane benactyzine), propanediol (mepropan) and trioxazin.

Hypnotic compounds (Phenobarbital for example) in small doses are also used as sedative drugs along with various neuroleptic agents (aminazine, tisercin) and some other compounds. Examples of such additional compounds include Bekhterev's mixture (sodium bromide, lychnis infusion, codeine phosphate), Corvalolum (ethyl ether of α-bromine isovaleric acid, monosodium salt of Phenobarbital, mint oil, ethyl alcohol, water), and Validol (menthol solution in menthyl valerate).

An example of a general sedative compound is shown in the U.S. Pat. No. 5,506,268 by Balandrin describing the use of isovaleramide as a mild anxiolytic and sedative agent.

The side effects of these medicinal preparations are a reduced ability to concentrate, drowsiness, and lower mental and physical effectiveness. In addition, patients often become dependent on a sedative in the course of treatment, reducing the desired effect, and a replacement sedative is needed to maintain the desired effect.

The need therefore exists for new sedative compounds that do not cause these side effects or drug dependency.

Pharmaceutical compounds used in treating patients with chemical and drug abuse define an important sub-category in the general area of sedative drugs. It is common knowledge that there are many individuals who become addicted to certain types of drugs taken either for medical reasons or for "recreational", non-medical use. Addiction, as has been defined by the Drug Addiction Committee of the National Research Council, is a state of periodic or chronic intoxication detrimental to the individual and produced by the repeated administration of a drug. Thus, an "addictive drug" as used herein is one that is initially used for any one of a number of purposes, e.g., for the relief of physical or psychic pain, and which if used consistently leads to dependency on the part of the individual taking the drug. The addicted individual develops a continuing craving for the drug and experiences withdrawal symptoms if an attempt is made to discontinue drug use. The terms "withdrawal syndrome" and "abstinence syndrome" are used to mean the same patient's condition for the purposes of this description.

Various pharmacological approaches for treating drug dependence have been tried. These approaches have typically involved attempts at treating the craving for the abused drug or alleviating the symptoms of withdrawal. The following references relate to some known methods and compositions for treating drug addiction and/or symptoms of withdrawal from drug dependency. U.S. Pat. No. 4,786,653 by Golwyn relates to the administration of phenelzine or an equivalent phenylalkylhydrazine, substances that are physiologically incompatible with addictive drugs such as amphetamines and cocaine. U.S. Pat. Nos. 1,796,977 and 1,782,111 describe the preparation of disulfiram ("Antabuse"), an alcohol deterrent. U.S. Pat. No. 4,696,818 by Kim relates to a method for alleviating symptoms associated with a variety of drugs, the method comprising administering an herbal composition to the drug dependent individual. U.S. Pat. No. 3,706,831 by Plotnikoff also describes a method for treating addiction to any one of a number of different types of drugs, which method involves administering to the addict a composition containing 2-imino-5-phenyl-4-oxazolidinone. U.S. Pat. Nos. 4,117,161 and 4,124,715 by Pozuelo disclose methods and compositions for treating withdrawal from narcotics and amphetamines which involve administration of alphamethyl-para-tyrosine or fusaric acid to the affected individual.

Treatment of nicotine withdrawal is described in the U.S. Pat. No. 4,325,952 by Baiocchi et al. and involves the use of a piperazine compound to treat the symptoms associated with withdrawal from nicotine. U.S. Pat. No. 4,788,189 by Glazer involves treatment of nicotine withdrawal by administration of clonidine in conjunction with a tricyclic antidepressant drug. U.S. Pat. No. 4,276,890 by Fichera describes a composition for alleviating symptoms of nicotine withdrawal by administering to the affected individual a composition containing a gamma-pyrone such as maltol or ethyl maltol.

Opioids and their numerous forms including opium, codeine, morphine, heroin etc. as well as its alkaloids and synthetic substitutes constitute a large segment of narcotics in general. Its use has become more widespread recently. The primary method of treatment for opium dependence is the discontinuation of narcotics and minimization of the abstinence syndrome. The only officially permitted method of discontinuation of narcotics involves the replacement from opioid receptors and the substitution of one of three possible ligands: 1. Antagonists of opioid receptors such as naltrexone, naloxone, nalmephine, and antaxone; 2. Agonists/antagonists such as pentazocine, butorphanol, nalbuphine, and buprenorphine aimed to activate receptors of a particular subtype such as kappa, while blocking receptors of another subtype such as mu; and 3. Agonists such as methadone and others that are better controlled and have a lower affinity to receptors, this method is called substitution therapy.

Each of these approaches has its own disadvantages. In the case of antagonists, there is no relief from the pain and other symptoms of withdrawal syndrome. The most severe, long-lasting manifestations of withdrawal syndrome cannot be eliminated either by initial general narcosis or with the assistance of anesthetics, tranquilizers, neuroleptics or antidepressants. These substances have numerous side effects while the incidence of relapse is rather high. With the use of agonists, the withdrawal syndrome is less pronounced; however, a dependence often develops on the medication that is also, in fact, a narcotic, although with a lower affinity to opioid receptors than, for instance, morphine or heroin. Besides, the duration of such substitution therapy is rather long, up to 3–6 months. Due to their psychological instability, drug addicts often "change their mind" and refuse treatment.

Therefore, a very substantial need in the art exists for a therapeutic method of treating drug abuse such that a drug-addicted individual is readily able to discontinue use of an abused drug without encountering the above-mentioned problems and withdrawal symptoms.

SUMMARY OF THE INVENTION

Accordingly, it is an object of the present invention to overcome these and other drawbacks of the prior art by providing a novel composition and a therapeutic method for causing a sedative effect without the known side effects of other known sedatives.

Its is also an object of the present invention to provide a novel composition and administration method for a longer lasting sedative and pain relief effect as compared with known pharmacological compounds.

It is another object of the present invention to provide a novel group of pharmaceutically acceptable compositions and a method of administration thereof capable of producing a ligand-receptor binding.

More specifically, the object of the invention is to provide a novel group of compositions and a method of their administration causing the activation of a signaling pathway that involves an opioid receptor but without causing a drug dependency of its own.

It is a further object of the present invention to provide a novel group of pharmaceutically acceptable compositions and a method of administration thereof for treatment of chemical and narcotics abuse.

It is yet a further object of the present invention to provide a novel group of pharmaceutically acceptable compositions and a method of administration thereof for treatment of patients addicted to opioids in all of their various natural and synthetic forms.

The compositions and method of the invention are based on a better understanding of the physiological role of the recently discovered cell membrane signaling mechanism, including opioid receptors and slow (tetrodotoxin resistant) sodium channels. A novel compound chosen from the group of gamma-pyrones was used to activate this cell membrane signaling mechanism. This group was chosen by taking into account the newly discovered mechanism of ligand-receptor binding occurring due to the formation of hydrogen bonds. These substances have their effect because the active centers of the molecule-agonist of the gamma-pyrone substance (when it is interacting with the active sites of the receptor) are located at the same distance from each other as the active atoms of morphine, which also forms hydrogen bonds with receptor.

One of the preferred compositions of the invention is comenic acid, which can be described as a 5-hydroxy-4-oxo-4H-pyran-2-carbon acid. It has been discovered that administration of this acid to animals at a specified dosage produces a desired sedative effect without causing drug dependency after a 50-day period of continued daily use. The effect is long lasting, up to 24 hours after administration. The effective dosage range was found to be from about 5 to about 200 milligrams of the acid per 1 kilogram of body weight of the subject. The acid can be administered in a number of pharmaceutically acceptable ways by mixing it with known and biologically acceptable carriers. Examples of administration modes include a direct intravenous injection, parenterally, inhaling of a powder or a spray, swallowing of a liquid or solid composition, peritoneal injection, transdermal or transmucosal penetration, etc. It was discovered that over a relatively short period of time, administration of the comenic acid in a pharmacologically effective dose as described above has provided a cure of narcotic dependency in animals. That effective duration of administration ranges from about 5 to about 30 days with a preferred duration from about 13 to about 20 days. This duration compares quite favorably to a typical drug abuse treatment cycle of 3 to 6 months.

Other compounds from a gamma-pyrone general group can also be used. Several of them have been already tried experimentally with promising results. Specific examples of other compounds usable for the purposes of this invention include meconic acid, 6-hydrocomenic acid, and chelidonic acid, as described in more detail below.

DETAILED DESCRIPTION OF THE PREFERRED EMBODIMENTS OF THE INVENTION

A new mechanism for causing sedation and for reducing anxiety, depression, and pain has been discovered recently. Morphine is one of the 20 alkaloids present in natural opium. It is the best known agonist of opioid receptors and triggers of sequence of intracellular signaling processes. The first step in this sequence is ligand-receptor binding, in which the target of morphine is a well-studied class of cell membrane receptors. Activation by morphine of opioid receptors, which are linked to ion channels, can produce analgesic and sedative effect. Opioids decrease pain sensitivity by reducing the calcium-dependent release of neuromediators from presynaptic terminals, thus inhibiting signal transmission between neurons. It has been recently published by the inventors of the present invention that there exists a previously unknown interaction between the morphine receptor $Na^+$, $K^+$-ATPase and the activation gating system of $TTX_r$-sodium channels (see B. V. Krylov et. al., *Russian J of Physiology* Vol. 85, No. 2, pages 225–236, 1999. English translation: Morphine Decreases the Voltage Sensitivity of Slow Sodium Channels, *Neuroscience and Behavioral Physiology*, Vol. 30, No. 4, 2000, pages 431–439). Therefore, there exists a newly discovered signaling pathway in the cell membrane of a sensory neuron (dorsal root ganglion cells).

The principle behind the present invention is to substitute morphine with a more friendly and benign compound, which is still capable of activating this newly discovered signaling pathway, thereby reducing pain and other negative effects of abstinence syndrome, but does not create dependency or euphoria associated with morphine and other opioid alkaloids.

The main known agonist of the mu-opioid receptor is morphine—a hydrophobic molecule. This molecule has a stiff structure with only 3 atoms potentially active to form hydrogen bonds—one nitrogen (N) atom and two oxygen (O) atoms. The bridging oxygen O atom between the two organic rings is not active. The oxygen O atom from the C—O—H group (connected with the aromatic ring) and the nitrogen N atom are involved in the formation of the hydrogen bonds. The distance between the nitrogen N atom and the active oxygen O atom is critical in the formation of hydrogen bonds between the receptor and the main agonist.

The receptor is activated only when two hydrogen bonds are formed therebetween, namely 1. The O—H group mentioned above (the aromatic ring helps to fix the molecule's position in interacting with the aromatic ring of the receptor binding site) and corresponding binding receptor site, and 2. The N atom with another corresponding binding receptor site.

According to the invention, similar to morphine, gamma-pyrone substances interact with this receptor, forming two hydrogen bonds and thus switching on the signaling pathway. The blocker molecule (naloxone or naltrexone) works when it occupies the position of the agonist molecule in the receptor, forming only one hydrogen bond with the O—H group connected with the aromatic ring. Again, the aromatic ring helps to fix the molecule's position in interacting with the aromatic ring of the receptor site.

Gamma-pyrone class of molecules as agonists realizes the mechanism of forming two hydrogen bonds forming during ligand-receptor interaction. When interacting with active sites of the receptor, these molecules take such form that the distance between the two active atoms approximates the distance between the atoms needed for formation of hydrogen bonds between the receptor and the main agonist. Thus, it can activate the receptor signaling pathway.

Gamma-pyrones are generally known to be used for medicinal purposes. They have been predominately used as food additives, viral agents (as described for example in the PCT publication No. WO 92/13850); for treatment of iron-deficiency anemia (see for example the U.S. Pat. No. 4,575,502); high blood sugar and diabetes (see for example U.S. Pat. No. 5,888,993), allergic conditions (see for example U.S. Pat. No. 4,198,426), and other ailments. They have never been suggested to be used for sedation or drug abuse related pain relief since there was no rationale known for doing so.

Comenic acid was found to be an excellent representative of a gamma-pyrone group in use for the purposes of the present invention. 5-hydroxy-4-oxo-4H-pyran-2-carbon acid, or comenic acid, exists in the form of yellow crystals, has a melting point of about 270° C., and has a molecular mass of $C_6H_4O_5$ equal to 156.095. Comenic acid is moderately hydro- and alcohol-soluble and practically insoluble in nonpolar organic solvents. Comenic acid is produced from kojic acid with good yield. Comenic acid is one of the ingredients of a widely used antibacterial medicinal preparation sold in Russia, Baliz-2. This suggests that it is non-toxic and pharmaceutically acceptable in certain dosages.

To demonstrate its sedative effect, comenic acid was compared to Valerian extract. The sedative effect was measured by the change in motor activity of male rats of Wistar line with the mass of 0.20–0.23 kg in "the open field" test [Guiding and Method Materials in Experimental and Clinical Study of New Drugs. Part 2.M., 1980, pp. 126–133]. The results of the tests are presented in the table 1 below.

Group 1—Control. Male rats were subjected to the enteral introduction of 0.5 ml of saline solution. Then, the animals were divided into two groups. The rats in the first group were tested in "the open field" 60 minutes after the solution's introduction. The rats in the second group were tested 90 minutes after the introduction. The test consisted of the rat being placed in the center of "the open field", and then the number of squares of "the open field" that the rat crosses within 5 minutes is counted (an estimation of motor activity).

Groups 2–5—Valerian extract. Valerian extract was steamed until it became dry. Then, the dry remains were dissolved in saline in the required dosage (see table 1 and rated in mg/kg of a rat's body weight). The solution obtained was introduced into rats in the same way as for control. The testing of rats in "the open field" was also carried out as described for control.

Groups 6–9—Comenic acid. Comenic acid was dissolved in saline in the desired dosages (see table 1 below). The solution's pH was adjusted to equal 6.5–6.8 using concentrated NaOH solution. Comenic acid was introduced into the rats in the same way as in control. The testing of rats in "the open field" was carried out as described for control group as well.

TABLE 1

INFLUENCE OF COMENIC ACID ON RATS' MOTOR ACTIVITY IN "THE OPEN FIELD" TEST

| No. | Experiment conditions | Dosage of medicinal preparation (mg/kg of body weight) | Motor activity after the preparation's introduction (n) | | Lowering motor activity relative to the control (%) | | Lowering motor activity relative to the Valerian extract (%) | |
|---|---|---|---|---|---|---|---|---|
| | | | 60 min | 90 min | 60 min | 90 min | 60 min | 90 min |
| 1 | Saline | 0 | 50.3 ± 7.8 | 47.5 ± 8.2 | | | | |
| 2 | Valerian | 1 | 53.9 ± 8.1 | ±9.8 | −7 | 11 | | |
| 3 | extract | 10 | 48.5 ± 10.2 | 38.1 ± 10.5 | 4 | 20 | | |
| 4 | | 50 | 38.9 ± 9.8 | 31.5 ± 5.8 | 23 | 38 | | |
| 5 | | 100 | 40.8 ± 4.5 | 21.8 ± 8.1 | 19 | 54 | | |
| 6 | Comenic | 1 | 43.9 ± 6.8 | 51.2 ± 8.3 | 13 | −8 | 19 | −21 |
| 7 | acid | 10 | 37.6 ± 5.9 | 41.6 ± 6.8 | 25 | 12.5 | 22 | −9 |

TABLE 1-continued

INFLUENCE OF COMENIC ACID ON RATS' MOTOR ACTIVITY IN
"THE OPEN FIELD" TEST

| Experiment | | Dosage of medicinal preparation (mg/kg of body weight) | Motor activity after the preparation's introduction (n) | | Lowering motor activity relative to the control (%) | | Lowering motor activity relative to the Valerian extract (%) | |
|---|---|---|---|---|---|---|---|---|
| No. | conditions | | 60 min | 90 min | 60 min | 90 min | 60 min | 90 min |
| 8 | | 50 | 18.7 ± 3.3 | 15.2 ± 3.1 | 63 | 68 | 52 | 52 |
| 9 | | 100 | 13.4 ± 4.8 | 10.3 ± 2.8 | 73 | 78 | 67 | 53 |

Results above indicate that the administration of comenic acid to Wistar male rats with a body weight of 200–230 g in dosage of 50 and 100 mg/kg of body weight has lowered their motor activity by 68% and 78%, respectively, as compared with the control group (saline), and 52 and 53%, respectively, as compared with the valerian extract. Therefore, the sedative effect of comenic acid was twice that of valerian extract in these experiments with rats.

These experiments were repeated with the same animals and resulted in good roducibility of results. Also, there were no side effects of the administration of comenic acid iced. In addition, there was no development of tolerance to comenic acid developed by the rats indicating that no drug dependency is expected.

Other preferred compounds selected from the same general gamma-pyrone group include 3-hydroxy-4-oxo-4h-pyran-2,6-dicarboxylic acid (also known as meconic acid or 3-hydroxy-4-pyrone-2,6-dicarboxylic acid); 6-hydrocomenic acid (which is a comenic acid with an OH group in position 6); 4-oxo-4h-pyran-2,6-dicarbonic acid (also referred to as chelidonic acid); and 3-hydroxy-2-methyl-4h-pyran-4on acid.

Utility and Mode of Administration:

The present invention is useful as a sedative and for effecting withdrawal from a wide range of drugs possessing addictive properties. The compositions of the invention are most useful in treating an individual withdrawing from narcotics, and more specifically from the use of opium alkaloids such as morphine, heroin and codeine, or from synthetic variations thereof.

It is intended that the selected gamma-pyrones as described in the proceeding section be administered as a substitute for the abused drug. Typically, this will involve administration of a therapeutically effective amount of a composition containing the compounds of the invention at least once every twenty-four hours. By "therapeutically effective amount" is intended a dosage quantity effective to significantly alleviate craving for the drug of abuse as well as reducing the intensity of or eliminating withdrawal symptoms associated with its discontinuance. The effective daily dosage range was found to be from about 5 to about 200 milligrams of the compound per kilogram of body weight of the subject, providing a therapeutically effective blood level of the compound. The lower limit of this effective daily dosage can be safely decreased all the way down to homeopathic concentrations while the upper limit can also be increased somewhat keeping in mind the limitations from the risks of over dosage. A reasonable lower limit may be set as low as about 0.03 milligram of the compound per kilogram of body weight of the subject. The preferred dosage range is from about 20 to about 100 mg per kilogram of body weight in one or several applications per day. That dosage can be achieved in a single application, multiple applications or as a continuous release application.

For use in human patients with an average weight ranging between 50 and 100 kg, the daily dosage is estimated to be from about 250 mg to about 50 g per patient per day. It should of course be adjusted individually based on the decision of a treating physician and depending on the actual body weight of the patient. That general recommendation takes into account some losses in the amount of active ingredient during the transmission into the blood stream. To allow for multiple applications per day ranging from 1 to 6, the active ingredient unit dosage content range is estimated to be from about 40 mg to about 50 g. The lower limit of this unit dosage can be also safely decreased down to homeopathic levels. A reasonable lower limit may be set as low as about 1 mg of the compound per unit dosage. In the preferred form, the unit dosage contains about 200 mg to about 20 g of the active ingredient mixed with a pharmaceutically acceptable carrier.

It was also found that daily administration of the compounds of the present invention to animals at a predetermined dosage produces a desired sedative effect without causing drug dependency after as long as 50 days of continued daily use and possibly longer. The effect from each administration is lasting up to 24 hours.

For treating drug abuse patients, it is suggested that effective duration of treatment ranges from about 5 days to about 30 days. The most preferred duration is from about 13 to about 20 days.

For example, an optimal regimen for parenteral administration will involve daily injection of an aqueous composition containing 5–200 mg/kg of a gamma-pyrone compound as described above.

Administration of the compounds described herein can be via any of the accepted modes of systemic administration for therapeutic agents. These methods include oral, rectal, parenteral, transdermal, transmucosal, subcutaneous implant and other systemic modes. The preferred methods of administration are parenteral, transmucosal, and a subcutaneous continuous release implant.

For solid compositions, e.g., for oral administration, the compounds will be formulated with pharmaceutical grades of acceptable carrier such as mannitol, lactose, starch, magnesium stearate, sodium saccharin, talc, cellulose, glucose, sucrose, magnesium carbonate, or the like. The compositions may also be formulated as suppositories using, for example, polyalkylene glycols (e.g., propylene glycol) as the carrier. Liquid pharmaceutically administerable compositions can be prepared by dissolving, suspending, dispersing, etc., the gamma-pyrones as described above and optional pharmaceutical carriers in an acceptable solution such as, for example, water, saline, aqueous dextrose, glycerol, ethanol, or the like, to thereby form a sterile and pyrogen-free solution or suspension. If desired, the pharmaceutical composition to be administered may also contain minor amounts of nontoxic auxiliary substances such as wetting or emulsifying agents, pH buffering agents or the like, e.g., sodium acetate, sorbitan monolaurate, triethanolamine sodium acetate, triethanolamine oleate, etc. Actual methods of preparing such dosage forms are known in the art, or will be apparent, to those skilled in the art; for example, see Remington's Pharmaceutical Sciences, Mack Publishing Co., Easton, Pa.

For oral administration, specifically, a pharmaceutically acceptable non-toxic composition is generally formed by the incorporation of any of the normally employed compounds described above. Such compositions can take the form of solutions, suspensions, tablets, pills, capsules, powders, sustained release formulations and the like. Such compositions can contain 1 wt. % to 95 wt. % active ingredients, preferably 1 wt. % to 70 wt. %.

Parenteral administration is generally characterized by injection either subcutaneously, intramuscularly, or intravenously. Injectables can be prepared in conventional forms, either as liquid solutions or suspensions, solid forms suitable for solution or suspension in liquid prior to injection, or as emulsions. Suitable excipients include, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, or the like.

A more recent approach for parenteral administration employs the implantation of a slow-release or sustained-release system, such that an approximately constant level of dosage is maintained. See, e.g., U.S. Pat. No. 3,710,795, the disclosure of which is incorporated by reference herein. This application is especially beneficial in a subcutaneous continuous release form for drug addicts. In that case, a single visit to a physician can result in a subcutaneous implant of a slow release substrate (similar to nicotine withdrawal implant strips such as "Norplant") providing a constant therapeutically effective level of a compound of the invention over the entire treatment period as described above. Also, unauthorized removal of an implant to stop the therapy is much harder to do for a drug addict than discontinue the medication delivered in other forms.

The compounds of the invention may also be delivered through the body surface, i.e., transdermally or transmucosally. By "transdermal" as used herein is meant passage into and through the skin to achieve effective therapeutic blood levels. "Transmucosal" is intended to mean passage through a mucosal membrane of a living organism and thus includes delivery of drugs through either nasal or buccal tissue. Transdermal or transmucosal delivery will involve topical application of the compounds of the invention in the form of an ointment, gel, cream, or the like, or may involve use of a drug delivery device as taught, for example, in U.S. Pat. Nos. 3,742,951, 3,797,494, or 4,568,343. Such compositions may optionally contain a permeation enhancer as known in the art, to increase the rate at which the compounds of the invention permeate through the skin or mucosal tissue.

Transmucosal administration of the present compositions is preferably effected transnasally, and more preferably by way of a nasal spray. Preferred vehicles for use in such a nasal spray are sterile saline solutions having a pH compatible with that of the nasal mucosa, and a particularly preferred vehicle for use herein is the nasal lubricant manufactured and sold under the trademark "Pretz" by Parnell Pharmaceuticals (San Rafael, Calif.), or a similar carrier.

Solid nasal powders or insufflations can also be used in a similar manner for transmucosal delivery. For such purpose, the compounds are administered in finely divided solid form together with a pharmaceutically accepted solid carrier. An example of such carrier is a finely divided polyethylene glycol ("Carbowax 1540") or finely divided lactose. Such compositions may also include other finely divided excipients.

For administering the compounds of the invention by inhalation of aerosol, the active ingredient compound is dissolved in a biocompatible liquid such as water, saline, or ethanol and mixed with a volatile propellant, for example dichlorotetrafluoroethane and dichlorodifluoromethane, and placed in a pressurized container having a metering valve to release a predetermined amount of material based on the guidelines described above.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for treatment of a subject with a neurotic disorder of a type being effected by modulation of a slow sodium channel signaling pathway involving ligand-receptor binding in the opioid receptor site area, said method including parenteral systemic administration of a therapeutically effective amount of a substance with sedative effect, said substance comprising a comenic acid gamma-pyrone compound and a pharmaceutically acceptable carrier, whereby said substance effects modulation of said signaling pathway without causing physical dependency associated with opiates wherein said neurotic disorder is pain.

2. The method as in claim 1, wherein said therapeutically effective amount defined as a daily dosage ranging from about 0.03 to about 200 mg of said gamma-pyrone per kilogram of body weight of said subject.

3. The method as in claim 2, wherein said daily dosage ranging from about 20 to about 100 mg of said gamma-pyrone per kilogram of body weight of said subject.

4. The method as in claim 1, wherein said neurotic disorder is pain associated with withdrawal syndrome in drug abuse treatment.

5. The method as in claim 4, wherein said drug is based on opioid and its alkaloids.

6. The method as in claim 5, wherein the duration of said treatment is from about 5 to about 30 days.

7. The method as in claim 6, wherein said duration is from about 13 to about 20 days.

* * * * *